United States Patent
Hendrix et al.

(10) Patent No.: US 6,660,331 B2
(45) Date of Patent: Dec. 9, 2003

(54) MOCVD OF SBT USING TOLUENE-BASED SOLVENT SYSTEM FOR PRECURSOR DELIVERY

(75) Inventors: Bryan C. Hendrix, Danbury, CT (US); Thomas H. Baum, New Fairfield, CT (US); Debra Desrochers Christos, Monroe, CT (US); Jeffrey F. Roeder, Brookfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 10/010,262

(22) Filed: Dec. 7, 2001

(65) Prior Publication Data

US 2002/0068129 A1 Jun. 6, 2002

Related U.S. Application Data

(60) Division of application No. 09/440,235, filed on Nov. 15, 1999, now Pat. No. 6,340,586, which is a continuation-in-part of application No. 09/224,614, filed on Dec. 31, 1998, now Pat. No. 6,111,124.

(51) Int. Cl.$^7$ ................................ C23C 16/40
(52) U.S. Cl. ..................... 427/255.23; 427/255.32; 427/255.36; 427/901
(58) Field of Search ............. 427/255.23, 255.32, 427/901, 255.36

(56) References Cited

U.S. PATENT DOCUMENTS

| | | | |
|---|---|---|---|
| 4,975,299 A | | 12/1990 | Mir et al. |
| 5,204,314 A | | 4/1993 | Kirlin et al. |
| 5,453,494 A | * | 9/1995 | Kirlin et al. .................. 534/15 |
| 5,478,610 A | | 12/1995 | Desu et al. |
| 5,629,229 A | * | 5/1997 | Si et al. ......................... 438/3 |
| 5,677,002 A | | 10/1997 | Kirlin et al. |
| 5,700,400 A | | 12/1997 | Ikai et al. |
| 5,820,664 A | | 10/1998 | Gardiner et al. |
| 5,859,274 A | | 1/1999 | Baum et al. |
| 5,900,279 A | * | 5/1999 | Hideaki et al. .......... 427/248.1 |
| 5,916,359 A | | 6/1999 | Baum et al. |
| 5,997,637 A | | 12/1999 | Ikai et al. |
| 6,111,124 A | | 8/2000 | Baum et al. |

OTHER PUBLICATIONS

U.S. patent application Ser. No. 08/975,087, Hintermaier et al., filed Nov. 20, 1997.

U.S. patent application Ser. No. 08/835,768, Baum et al., filed Apr. 8, 1997.

U.S. patent application Ser. No. 08/484,654, Gardiner et al., filed Jun. 7, 1995.

Ami, et al., Materials Research Society Symposium Proceedings, vol. 415, 1996, pp. 195–200.

* cited by examiner

*Primary Examiner*—Timothy Meeks
(74) *Attorney, Agent, or Firm*—Margaret Chappuis (57) ABSTRACT

A solvent composition useful for liquid delivery MOCVD, comprising toluene and a Lewis base, wherein toluene is present at a concentration of from about 75% to about 98% by volume, based on the total volume of toluene and the Lewis base. Such solvent composition is usefully employed to dissolve or suspend precursors therein for liquid delivery MOCVD, e.g., MOCVD of ferroelectric material films such as SBT.

25 Claims, 5 Drawing Sheets

MOCVD OF SBT USING TOLUENE-BASED SOLVENT SYSTEM FOR PRECURSOR DELIVERY

This is a divisional of application Ser. No. 09/440,235, filed on Nov. 15, 1999, now U.S. Pat. No. 6,340,586, which is a continuation-in-part of U.S. patent application Ser. No. 09/224,614, filed Dec. 31, 1998 in the names of Thomas H. Baum and Raymond H. Dubois for "Lewis Base Adducts of Anhydrous Mononuclear Tris β-diketonate Bismuth Compositions for Deposition of Bismuth-containing Films, and Method of Making the Same" now U.S. Pat. No. 6,111,124.

BACKGROUND OF THE INVENTION

1. Field of the Invention

This invention relates to metalorganic chemical vapor deposition (MOCVD) of strontium bismuth tantalate, and in particular to a toluene-based solvent system for precursor delivery for MOCVD of such material

2. Description of the Related Art

Liquid delivery MOCVD is the preferred method for depositing thin films of ferroelectric materials because of the ability to carefully control composition and deposit conformal films of high density. In such a process a solution or suspension of precursors (metalorganic source reagents for the respective metal components of the product film material) is vaporized, preferably at high rate by "flash vaporization" techniques to produce a corresponding precursor vapor which may be mixed with carrier and/or additive gases (e.g., oxygen-containing gas, inert gases such as argon, helium, etc., co-reactive gases, diluents, etc.) to form a vapor mixture. The vapor mixture then is flowed to a deposition zone where the precursor mixture is contacted with a substrate at elevated temperature to effect deposition from the vapor phase onto the substrate of a desired material.

MOCVD of $SrBi_2Ta_2O_9$ (SBT) and related materials use precursors that are chemically compatible in solution for long periods of time and also have similar decomposition characteristics vis-à-vis one another in the MOCVD process. $Sr(thd)_2$-LBA, $Bi(thd)_3$, and $Ta(O-i-Pr)_4(thd)$ (where thd stands for 2,2,7,7-tetramethyl-3,5-heptanedionato, LBA stands for a Lewis base adduct and O-i-Pr stands for isopropoxide) provide a preferred combination of precursors for such purpose. Precursors for deposition of SBT and other ferroelectric materials, and their use in liquid delivery MOCVD formation of high quality product films, are more fully described in U.S. patent application Ser. No. 08/960,915 filed Oct. 30, 1997 in the names of Thomas H. Baum, et al., now issued as U.S. Pat. No. 5,859,274, and U.S. patent application Ser. No. 08/976,087 filed Nov. 20, 1997 in the names of Frank S. Hintermaier, et al.

The best previously known solvent system for this precursor suite (of $Sr(thd)_2$-LBA, $Bi(thd)_3$, and $Ta(O-i-Pr)_4(thd)$) consisted of alkanes and in particular a mixture of octane, decane, with an excess of the LBA of the strontium precursor, $Sr(thd)_2$. In particular, a ratio of 5 parts octane, 4 parts decane, and 1 part LBA was found to maintain the precursors in a stable condition and deliver them reliably to a flash vaporization equipment. Solvent compositions of such type are more fully described in U.S. patent application Ser. No. 08/975,372 filed Nov. 20, 1997 in the names of Thomas H. Baum, et al., now issued as U.S. Pat. No. 5,916,359.

However, the alkane-based solvents have limited solubility of the aforementioned SBT precursors, especially for the $Sr(thd)_2$, which only dissolves to about 0.2 M in a 5:4:1 mixture of octane:decane:pmdeta. This limited solubility characteristic of the solvent composition has disadvantages for liquid delivery vaporization and the subsequent deposition process. During vaporization, wherein the precursor solution typically is flowed through a liquid delivery tube to a heated surface, the molarity of the precursor solution must remain significantly below the solubility limit to prevent precipitation of solid metalorganic particles from the solution, which would otherwise occur as solvent boils off in the liquid delivery tube, and which would lead to clogging of the liquid delivery tube. In addition, low solution molarity requires the vaporization of more solvent in order to deliver the same amount of precursor to the process. This creates undue requirements for the supply of heat to the metalorganics in the vaporizer, since more heat must then be provided to volatilize the additional solvent that is present.

The deposition process itself also is adversely affected by low molarity solutions. By way of example, film growth rates were limited to 3–4 nanometers per minute (nm/min) in a prototype MOCVD reactor delivering a 0.30M solution at a rate of 0.2 ml/min. Growth rates should be 2–3 times higher than this level in order to meet the requirements of a "manufacturable process." In addition, limiting the rate of delivery of precursor to the substrate surface makes it more difficult to push the process into a surface kinetic-controlled growth regime where conformality to non-planar structures is improved, relative to film formation processes operating outside of such regime.

It would therefore be an advance in the art to provide a solvent medium for liquid delivery MOCVD of precursor compositions such as SBT, which overcome the aforementioned difficulties.

SUMMARY OF THE INVENTION

The present invention relates to a solvent composition that is usefully employed for liquid delivery MOCVD applications, e.g., as a solvent medium for SBT, doped SBT and other ferroelectric precursors.

In one aspect, the invention relates to a solvent composition useful for liquid delivery MOCVD, comprising toluene and a Lewis base, wherein toluene is present at a concentration of from about 75% to about 98% by volume, based on the total volume of toluene and the Lewis base.

Another aspect of the invention relates to a precursor composition useful for liquid delivery MOCVD, comprising (i) a solvent composition including toluene and a Lewis base, wherein toluene is present at a concentration of from about 75% to about 98% by volume, based on the total volume of toluene and the Lewis base, and (ii) a precursor species dissolved or suspended in the solvent composition.

A still further aspect of the invention relates to a method of forming a material film on a substrate, comprising:

providing a precursor composition for at least one component of the material film; volatilizing the precursor composition to yield a precursor vapor; and contacting the precursor vapor with the substrate to deposit said at least one component of the material film thereon;

wherein the precursor composition comprises (i) a solvent composition including toluene and a Lewis base, wherein toluene is present at a concentration of from about 75% to about 98% by volume, based on the total volume of toluene and the Lewis base, and (ii) a precursor species dissolved or suspended in the solvent composition.

Other objects, features and advantages of the invention will be more fully apparent from the ensuing disclosure and appended claims.

DETAILED DESCRIPTION OF THE INVENTION, AND PREFERRED EMBODIMENTS THEREOF

The disclosures of the following U.S. patents and patent applications which are commonly owned by assignee of the present application, are hereby incorporated herein by reference in their entireties:

U.S. patent application Ser. No. 08/835,768 filed Apr. 8, 1997 in the names of Thomas H. Baum, et al., now U.S. Pat. No. 5,919,522;

U.S. patent application Ser. No. 08/484,654 filed Jun. 7, 1995 in the names of Robin A. Gardiner et al., now U.S. Pat. No. 6,110,529;

U.S. patent application Ser. No. 08/307,316 filed Sep. 16, 1994 in the names of Peter S. Kirlin et al., now issued as U.S. Pat. No. 5,679,815;

U.S. patent application Ser. No. 08/453,380 filed May 30, 1995 in the names of Peter S. Kirlin et al., now issued as U.S. Pat. No. 5,677,002;

U.S. patent application Ser. No. 08/414,504 filed Mar. 31, 1995 in the names of Robin A. Gardiner et al., now issued as U.S. Pat. No. 5,820,664;

U.S. application Ser. No. 08/280,143 filed Jul. 25, 1994, in the names of Peter S. Kirlin, et al., now U.S. Pat. No. 5,536,323;

U.S. patent application Ser. No. 07/927,134, filed Aug. 7, 1992 in the names of Peter S. Kirlin, et al., now abandoned;

U.S. patent application Ser. No. 07/807,807, filed Dec. 13, 1991 in the names of Peter S. Kirlin, et al., now issued as U.S. Pat. No. 5,204,314;

U.S. application Ser. No. 08/181,800 filed Jan. 15, 1994 in the names of Peter S. Kirlin, et al., and issued as U.S. Pat. No. 5,453,494;

U.S. application Ser. No. 07/918,141 filed Jul. 22, 1992 in the names of Peter S. Kirlin, et al., and issued Jan. 18, 1994 as U.S. Pat. No. 5,280,012;

U.S. application Ser. No. 07/615,303 filed Nov. 19, 1990 in the names of Peter S. Kirlin, et al., now abandoned;

U.S. application Ser. No. 07/581,631 filed Sep. 12, 1990 in the names of Peter S. Kirlin, et al., and issued Jul. 6, 1993 as U.S. Pat. No. 5,225,561;

U.S. patent application Ser. No. 07/549,389 filed Jul. 6, 1990 in the names of Peter S. Kirlin, et al.;

U.S. patent application Ser. No. 08/975,372 filed Nov. 20, 1997 in the names of Thomas H. Baum, et al., now issued as U.S. Pat. No. 5,916,359;

U.S. patent application Ser. No. 08/960,915 filed Oct. 30, 1997 in the names of Thomas H. Baum, et al., now issued as U.S. Pat. No. 5,859,274; and U.S. patent application Ser. No. 08/976,087 filed Nov. 20, 1997 in the names of Frank S. Hintermaier, et al., currently pending.

The present invention is based on the discovery of a toluene based solvent system, which in application to the MOCVD of SBT, has high solubility of all precursor components, no undesired chemical interactions in solution, and displays utility in the CVD of high purity SBT films.

For example, as applied to the MOCVD of SBT using the aforementioned preferred precursor combination of $Sr(thd)_2$-LBA, $Bi(thd)_3$, and $Ta(O-i-Pr)_4(thd)$, it was found that the solubility of $Bi(thd)_3$ increased from 0.75M to 1M as the ratio of toluene:pmdeta (the Lewis base "pmdeta" is pentamethyldiethylenetriamine) changed from 25:1 to 10:1. This data is summarized in Table I below.

TABLE I

Solubility of SBT preferred precursors in various solvent systems.

| | 5:4:1 octane:decane:pmdeta | 25:1 toluene:pmdeta | 10:1 toluene:pmdeta |
|---|---|---|---|
| Boiling point | 125–127° C. | 110.6° C. | 110.6° C. |
| $Sr(thd)_2$-pmdeta | 0.20M | 1.00M | 1.00M |
| $Bi(thd)_3$ | 0.50M | 0.75M | 1.00M |
| $Ta(O-i-Pr)_4(thd)$ | 1.00M | 0.50M | 0.50M |

Vaporization of the SBT preferred precursors in the 10:1 toluene:pmdeta solution at 0.3 total solution molarity and 0.30 ml/min gave vaporizer mean time to service (MTS) similar to the 5:4:1 octane:decane:pmdeta. The mean time to service is a measure of the extent of premature decomposition of the precursors in the vaporizer, the occurrence of side reactions in the vaporizer, and unwanted deposition of solids and viscous byproducts in the vaporizer. Thus, the "cleaner"

the vaporization operation in the heated vaporizer zone, the longer will be the MTS for the system. It is highly desirable to achieve MTS values as high as possible (i.e., the longest possible time between maintenance events for the vaporizer), since this maximizes on-stream time and equipment utility, and minimizes operating costs of the liquid vaporization MOCVD system, leading to a lower cost of ownership.

The above-tabulated results achieved by high toluene content solvent compositions for the MOCVD of SBT, viz., vaporization of the SBT preferred precursors in the 10:1 toluene:pmdeta solution at 0.3 total solution molarity and 0.30 ml/min yielding vaporizer MTS values similar to the use of 5:4:1 octane:decane:pmdeta solvent compositions for the same preferred SBT precursors, indicates that there are no adverse affects from the solvent system change. Despite the lower boiling point of the toluene solvent, there was surprisingly and unexpectedly no evidence of problems with precipitation from solvent boil-off in the delivery tube.

As an example of the use and benefits of toluene-enhanced solvent compositions of the present invention for MOCVD of SBT using the aforementioned preferred precursors of Sr(thd)$_2$-LBA, Bi(thd)$_3$, and Ta(O-i-Pr)$_4$(thd), a liquid delivery MOCVD SBT process was conducted using 10:1 toluene:pmdeta solvent at 0.3M total solution molarity and at 0.5M total solution molarity. It was found that the 0.5 M solution enabled growth rates to be achieved that were nearly double those obtained for the 0.3M solution, thereby evidencing that the process is limited by precursor delivery to the growth surface.

From corresponding experiments in 5:4:1 solvent compositions of octane:decane:pmdeta, it was demonstrated that increased precursor delivery increases the growth rate of the films in the mass-transport controlled regime, and increases both the growth rate and the conformality of films when altering the process from being limited by mass-transport kinetics to being limited by surface reaction kinetics.

It was also demonstrated that the higher molarity solutions in 10:1 toluene:pmdeta lead to higher delivery rates of precursors and higher growth rates.

The invention therefore contemplates a solvent composition that is unexpectedly superior for liquid delivery of precursors for SBT, such as the preferred Sr(thd)$_2$-LBA, Bi(thd)$_3$, and Ta(O-i-Pr)$_4$(thd) precursors, that is readily formulated and permits high delivery rates and high growth rates to be achieved which provide a "manufacturable process" for thin film deposition of SBT by liquid delivery MOCVD techniques.

Further, the invention contemplates a solvent composition that is also unexpectedly superior for liquid delivery of precursors for SBT, using the precursors Sr(thd)$_2$-LBA, Bi(thd)$_3$-LBA, and Ta(O-i-Pr)$_4$(thd) precursors, that is readily formulated and permits high delivery rates and high growth rates to be achieved which provide a "manufacturable process" for thin film deposition of SBT by liquid delivery MOCVD techniques.

Further, the invention contemplates a solvent composition that is unexpectedly superior for liquid delivery of precursors for doped SBT, such as Niobium doped SBT, wherein the preferred Sr(thd)$_2$-LBA, Bi(thd)$_3$, and Ta(O-i-Pr)$_4$(thd) precursors as well as a dopant precursor, e.g., Nb(O-i-Pr)$_4$ (thd), are readily formulated and permit high delivery rates and high growth rates to be achieved which provide a "manufacturable process" for thin film deposition of doped SBT by liquid delivery MOCVD techniques The solvent composition of the invention comprises toluene and a Lewis base, wherein toluene is present at a concentration of from about 75% to about 98% by volume, based on the total volume of toluene and the Lewis base.

In application to the liquid delivery MOCVD of SBT films, toluene preferably is present at a concentration of from about 90% to about 97% by volume, based on the total volume of toluene and Lewis base. Such solvent composition may for example have a boiling point in the range of from about 109.5 to about 112.0° C. In a particular embodiment for liquid delivery MOCVD of SBT, the volumetric ratio of toluene to the Lewis base is about 10:1 or about 91% by volume toluene and about 9% by volume Lewis base.

The solvent composition may comprise any suitable Lewis base, as for example a Lewis base comprising at least one of the following:

(a) amines and polyamines;
(b) N, S and O-containing aromatics;
(c) ligands of the formula:

wherein:
G is —O—, —S—, or —NR—, wherein R is H or hydrocarbyl;
(d) crown ethers;
(e) thioethers;
(f) ammonia and other nitrogenous species; and
(g) species of the formula: $R^0O(C(R^1)_2C(R^2)_2O)_nR^0$
wherein:
$R^0$=H, methyl, ethyl, n-propyl, cyanato, perfluoroethyl, perfluoro-n-propyl, or vinyl;
$R^1$=H, F, or a sterically acceptable hydrocarbyl substituent;
$R^2$=H, F, or a sterically acceptable hydrocarbyl substituent;
n=2, 3, 4, 5, or 6; and
each $R^0$, $R^1$, and $R^2$ may be the same as or different from the other $R^0$, $R^1$, and $R^2$, respectively.

Preferred Lewis base species of such type include:
polyamines;
pyridines;
bipyridines;
alkylpyridines;
ammonia;
crown ethers; and
species of the formula: $R^0O(C(R^1)_2C(R^2)_2O)_nR^0$
wherein:
$R^0$=H, methyl, ethyl, n-propyl, cyanato, perfluoroethylperfluoro-n-propyl, or vinyl;
$R^1$=H, F, or a sterically acceptable hydrocarbyl substituent;
$R^2$=H, F, or a sterically acceptable hydrocarbyl substituent;
n=2, 3, 4, 5, or 6; and
each $R^0$, $R^1$, and $R^2$ may be the same as or different from the other $R^0$, $R^1$, and $R^2$, respectively.

Particularly preferred Lewis base species include tetraglyme, tetrahydrofuran, bipydridine, ammonia, pyridine, alkylpyridine, 3-picoline, 18-crown-6 ethers, and amines/polyamines, e.g., pentamethyldiethylenetriamine (PMDETA), diethylenetriamine (DETA), tetraethylenepentaamine (TEPA) and hexamethyltetraethylenepentaamine (HMTEPA).

A precursor composition useful for liquid delivery MOCVD may comprise the aforementioned solvent composition and a precursor species dissolved or suspended in the solvent composition. Such precursor species may include a precursor for a metal of a ferroelectric material, e.g., a precursor for strontium and/or bismuth and/or tantalum and/or niobium Specific precursor species include $Sr(thd)_2$-LBA, $Bi(thd)_3$, $Bi(thd)_3$-LBA, $Ta(O-i-Pr)_4(thd)$ and $Nb(O-i-Pr)_4(thd)$, where LBA is a Lewis base adducting species. The Lewis base adducting species may suitably be the same as the Lewis base of the solvent composition.

In a preferred aspect, the precursor species comprise $Sr(thd)_2$-LBA, $Bi(thd)_3$, and $Ta(O-i-Pr)_4(thd)$, where LBA is a Lewis base adducting species that coordinatively complexes with $Sr(thd)_2$. Such a precursor composition may have a total solution molarity of from about 0.3 M to about 0.7 M.

The above-described precursor composition may be utilized in a liquid delivery MOCVD method of forming a material film on a substrate, comprising the steps of: providing a precursor composition for at least one component of the material film; volatilizing the precursor composition to yield a precursor vapor; and contacting the precursor vapor with the substrate to deposit said at least one component of the material film thereon.

In another aspect, the precursor species comprise $Sr(thd)_2$-LBA, $Bi(thd)_3$, $Ta(O-i-Pr)_4(thd)$ and $Nb(O-i-Pr)_4(thd)$ where LBA is a Lewis base adducting species that coordinatively complexes with $Sr(thd)_2$. Such a precursor composition may have a total solution molarity of from about 0.3 M to about 0.7 M.

In another aspect, the precursor species comprise $Sr(thd)_2$-LBA, $Bi(thd)_3$-LBA, $Ta(O-i-Pr)_4(thd)$ and $Nb(O-i-Pr)_4(thd)$ where LBA is a Lewis base adducting species that coordinatively complexes with $Sr(thd)_2$. Such a precursor composition may have a total solution molarity of from about 0.3 M to about 0.7 M.

The Lewis base component of the solvent composition of the invention may comprise any suitable Lewis base species that is compatible with the precursors that are employed in the corresponding precursor composition (including the solvent composition and the solute precursor species, e.g., metalorganic compounds or complexes for the metal components of the film to be formed by MOCVD using such precursor composition). The Lewis base may include Lewis base species that are selected to form adducts or coordination complexes with one or more of the precursor species.

The solvent composition of the invention may be readily formulated by simple mixing at ambient (room temperature) conditions of the respective toluene and Lewis base components.

The relative proportions of toluene and the Lewis base in respect of one another may be any suitable proportion that produce a metal-containing film with the desired characteristics when the precursor(s) of interest are dissolved or suspended therein and the resultant precursor composition is utilized for liquid delivery MOCVD.

For utilization in the liquid delivery MOCVD of SBT and other ferroelectric materials, the solvent compositions of the invention suitably comprise toluene and a Lewis base, wherein toluene is present at a concentration of from about 75% to about 98% by volume, based on the total volume of toluene and the Lewis base. As used in such context, of the Lewis base being a component of the solvent composition of the invention, the term "Lewis base" is intended to be broadly construed to include a single Lewis base species, as well as to encompass multiple Lewis base species as the Lewis base component of the solvent composition.

In the case of preferred precursor combination of $Sr(thd)_2$-LBA, $Bi(thd)_3$, and $Ta(O-i-Pr)_4(thd)$, the solvent composition is desirably formulated so that the volumetric ratio of toluene to the Lewis base is about 10:1 or about 91% by volume toluene and about 9% by volume Lewis base.

The solvent composition after its formulation may be mixed with the precursor components under gentle mixing, e.g., with a mechanical agitator, inert gas sparger, static mixer, or other mixer device or method, to place the precursor components in solution or suspension in the solvent medium, and thereby form the precursor composition, as a source material for liquid delivery MOCVD.

The precursor composition comprising the solvent composition and the dissolved or suspended precursor species therein then can be disposed in a supply vessel or feed liquid reservoir of a liquid delivery MOCVD system for the formation of a material on a substrate in a CVD reactor at suitable process conditions. The process conditions will depend on the specific material being deposited on the substrate, the configuration and geometry of the reactor, the precursor composition employed, and the rate of film growth being effected. The process conditions may readily be determined by suitable empirical approaches without undue experimentation, to determine appropriate temperatures, pressures, flow rates and compositional character of process streams.

The liquid delivery MOCVD system may comprise a system of the type disclosed in U.S. Pat. No. 5,204,314 issued Apr. 20, 1993 to Peter S. Kirlin et al. and in U.S. Pat. No. 5,536,323 issued Jul. 16, 1996 to Peter S. Kirlin et al., which describe heated vaporization structures such as microporous disk elements. In use, liquid source reagent compositions are flowed onto the vaporization structure for flash vaporization. Vapor thereby is produced for transport to the deposition zone, e.g., a CVD reactor. The liquid delivery systems of these patents provide high efficiency generation of vapor from which films may be grown on substrates.

The precursor vapor then is transported to a chemical vapor deposition zone containing a substrate, e.g., a wafer provided on a heated susceptor. Upon contacting of the precursor vapor with the wafer, the metal components of the vapor are deposited on the wafer surface. The vapor may be delivered in the chemical vapor deposition chamber by a disperser such as a showerhead or nozzle, to provide a uniform flux of the vapor across the width of the wafer, to yield a correspondingly uniform thickness of deposited metal-containing film on the wafer. The process conditions (temperature, pressure, flow rate and composition of the vapor) may be suitably controlled to ensure an optimum process result for the MOCVD operation being conducted in the process system.

The liquid delivery process utilizing precursor compositions of the invention to form a product material on a substrate therefore includes the steps of:

provyding precursor species for at least one of the components of the product film to be formed on the substrate and solubilizing or suspending same in a solvent composition according to the invention to form a precursor composition comprising such precursor species and the solvent composition;

vaporizing the precursor composition to form corresponding precursor vapor; and contacting the precursor vapor with a substrate to deposit the product material thereon.

The advantages of the invention include the following:

(1) the toluene based solvents of the invention have increased solubility for the metalorganic precursors that are preferred for the deposition of $SrBi_2Ta_2O_9$ ceramics and derivatives thereof;

(2) the increased solubility allows more robust vaporization, increasing the resistance of the solution to delivery tube clogging in the liquid delivery apparatus;

(3) the increased concentration of metalorganic precursors in the toluene based solvent allows for vaporization of the precursors with less heat load from evaporating solvent;

(4) the increased concentration of metalorganic precursor in the toluene based solvent increases the growth rate of the film leading to a more manufacturable process; and (5) the increased concentration of metalorganic precursor in the toluene based solvent increases the conformality of the films to non-planar structures leading to better performance of the product microelectronic device, e.g., ferroelectric capacitor.

The features and advantages of the invention are more fully shown with reference to the following non-limiting examples.

EXAMPLE 1

Experiments were performed using (1) a baseline 5:4:1 solvent system with a total precursor molarity of 0.20, (2) a 10:1 toluene:pmdeta solvent with the concentrations of each metalorganic fixed at the same values with a total solution molarity of 0.3M, and (3) a 10:1 toluene:pmdeta solvent with the concentrations of each metalorganic fixed at the same values with a total precursor molarity of 0.5.

The liquid delivery system used in these experiments was a Sparta™ 450 liquid delivery system (commercially available from Advanced Technology Materials, Inc., Danbury, Conn.) equipped with a ½" vaporizer. The liquid delivery system was attached to a 5" diameter quartz tube reactor as the MOCVD deposition chamber, and such reactor was equipped with temperature controls for independent control of reactor wall temperature and substrate temperature. For films grown in the mass transport limited regime, this reactor enabled growth rates about 3 times greater than the prototype MOCVD reactor mentioned in the Background of the Invention section hereof.

Experiments using 0.2M solution in 5:4:1 solvent showed (1) that the film growth rate was controlled by the rate of delivery of precursor to the surface and (2) that faster precursor delivery to the surface increased conformality.

Figure 1:
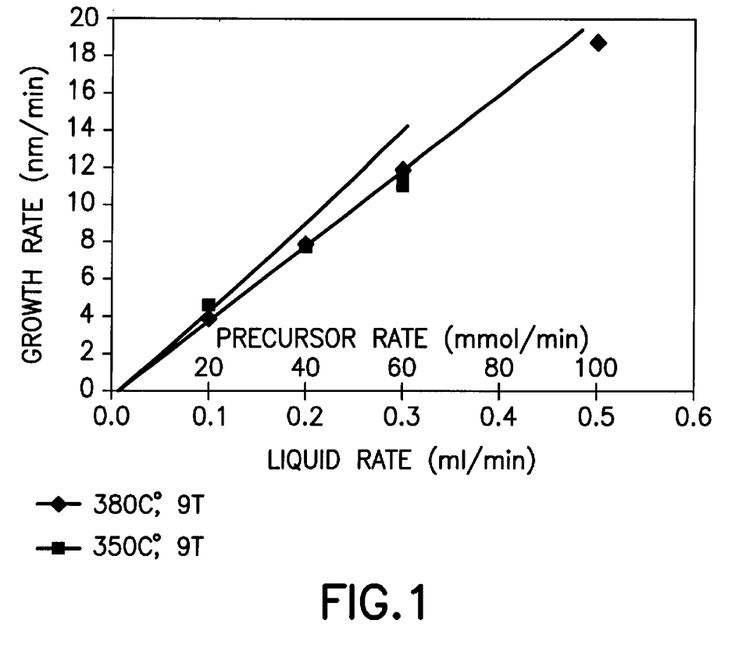
FIG. 1 is a graph of the growth rate of an SBT film as a function of liquid delivery rate for 9 Torr processes at 380° C. and 350° C. using 0.2M solution in 5:4:1 octane:decane:pmdeta.

FIG. 1 shows the growth rate of SBT films as a function of liquid delivery rate for 9 Torr processes at 380° C. and 350° C. using 0.2M solution in 5:4:1 octane:decane:pmdeta. Lines indicating a linear proportional increase in growth rate are shown for comparison to the measured increase in growth rate.

Two different growth temperatures were used at a process pressure of 9 Torr and 76% $O_2$. At 380° C., the growth rate increases linearly proportionally with the liquid delivery rate up to 60 mmol/min. The drop-off at 0.5 ml/min is attributed to either the onset of surface reaction limitation or a limitation in the vaporizer's ability to completely vaporize the liquid. At 380° C., the conformality of 1 μm wide by 1 μm deep trenches was 20–30% independent of growth rate.

At 350° C., the growth rate is less than linearly proportional to the liquid delivery rate, but still increases by more than a factor of 2 for a factor of 3 increase in precursor delivery rate. Also, the conformality of the same 1×1 μm trench structures was 30% at 20 mmol/min and 70–80% at 60 mmol/min. This indicates that at the lower temperature, the growth rate becomes dependent upon the surface reaction kinetics in addition to the rate of precursor delivery to the surface, and that as the delivery rate increases, the conformality improves. The data show that there was no growth rate penalty incurred in the lower temperature process.

Figure 2:
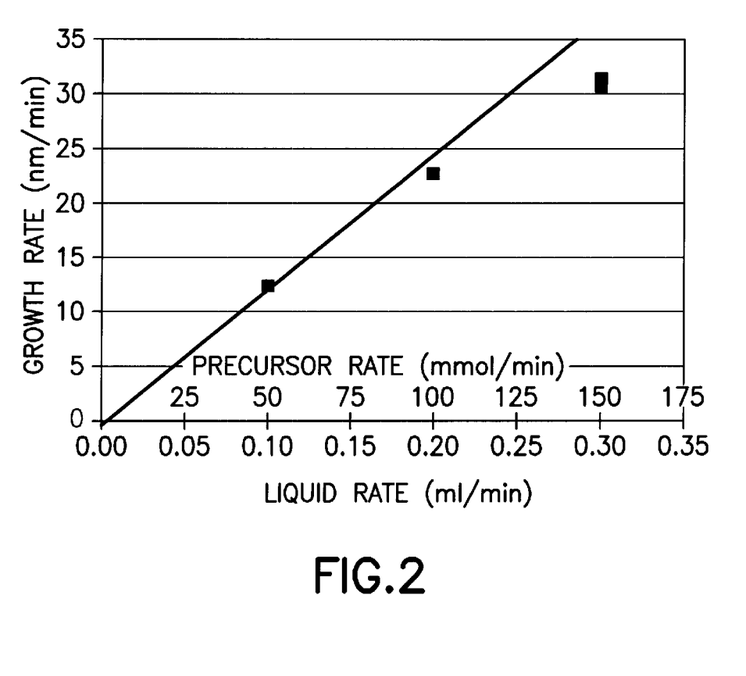
FIG. 2 is a graph of growth rate of an SBT film as a function of liquid delivery rate for 0.5M solution in 10:1 toluene:pmdeta at 380° C. and 9 Torr.

Next, experiments were performed with 0.3M and 0.5M solutions in 10:1 toluene:pmdeta. FIG. 2 is a graph of growth rate as a function of precursor liquid delivery rate for 0.5M solution in 10:1 toluene:pmdeta at 380° C. and 9 Torr. At a liquid delivery rate of 0.1 ml/min, the delivery of precursors increased by a factor of 2.5 over the 0.2M solution (from 20 mmol/min to 50 mmol/min), and the growth rate increased by a factor of about 3. The growth rate was no longer proportional to liquid delivery rate at this temperature. Conformality was not tested under these conditions, and it therefore is difficult to determine whether this deviation from linear proportionality reflects movement into the surface reaction controlled growth regime or simply a decrease in vaporization efficiency from the higher heat load of evaporating the precursors at a higher rate. In either case, it is clear that precursor was delivered to the substrate surface at a higher rate with the increase in solution concentration. There was no growth rate penalty incurred in going to the lower temperature process for the higher concentration (molarity) solution.

EXAMPLE 2

A 10:1 toluene: pmdeta solvent composition was made up and utilized for dissolution therein of SBT precursors $Sr(thd)_2$-LBA, $Bi(thd)_3$, and $Ta(O-i-Pr)_4(thd)$ wherein the LBA was pmdeta.

The solution had a total molarity of 0.3 M, comprising 0.128 M strontium, 0.099 M bismuth and 0.073 M tantalum.

A liquid delivery MOCVD system of the type described in Example 1 was employed to deposit films of SBT, at a precursor delivery rate of 0.10 milliliters per minute (ml/min), and oxygen was introduced as a carrier gas to the vaporizer so that the precursor vapor mixture (precursor vapor+carrier gas) contained 76% $O_2$ by volume, and an SBT film was deposited on a substrate in the MOCVD reactor.

The data generated in the runs are shown in the graphs of FIGS. 3–6.

Figure 3:
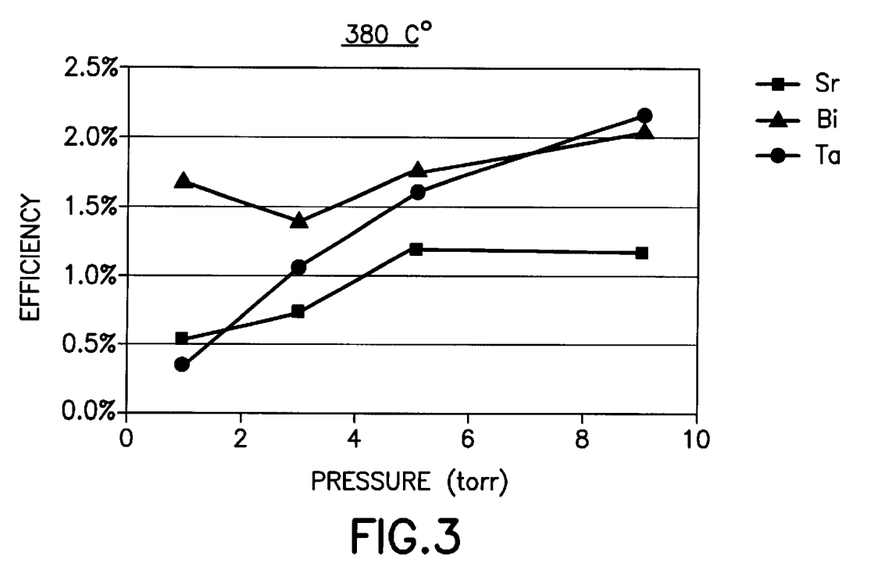
FIG. 3 shows film incorporation efficiency of Sr, Bi and Ta, as a function of pressure (Torr) at 380° C. for precursor solutions of 10:1 toluene: pmdeta solvent containing the precursors $Sr(thd)_2$-LBA, $Bi(thd)_3$, and $Ta(O-i-Pr)_4(thd)$.
Figure 4:
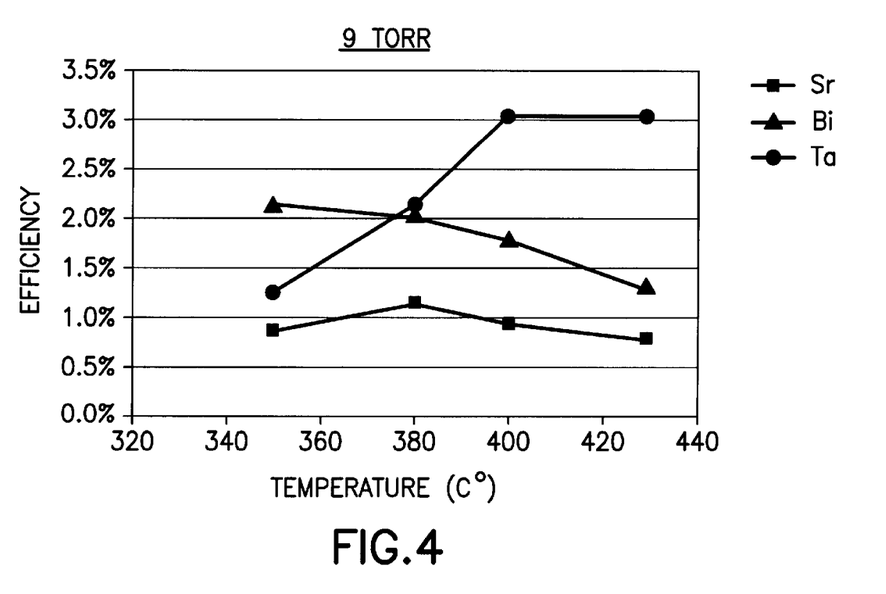
FIG. 4 is a graph of incorporation efficiency of Sr, Bi and Ta, as a function of temperature at 9 Torr for precursor solutions of 10:1 toluene: pmdeta solvent containing the precursors $Sr(thd)_2$-LBA, $Bi(thd)_3$, and $Ta(O-i-Pr)_4(thd)$.

FIG. 3 shows film incorporation efficiency of Sr, Bi and Ta, as a function of pressure (Torr) at 380° C. for precursor solutions of 10:1 toluene: pmdeta solvent containing the precursors $Sr(thd)_2$-LBA, $Bi(thd)_3$, and $Ta(O-i-Pr)_4(thd)$. FIG. 4 is a corresponding plot of incorporation efficiency of Sr, Bi and Ta, as a function of temperature at 9 Torr for precursor solutions of 10:1 toluene: pmdeta solvent containing the precursors $Sr(thd)_2$-LBA, $Bi(thd)_3$, and $Ta(O-i-Pr)_4$(thd).

Figure 5:
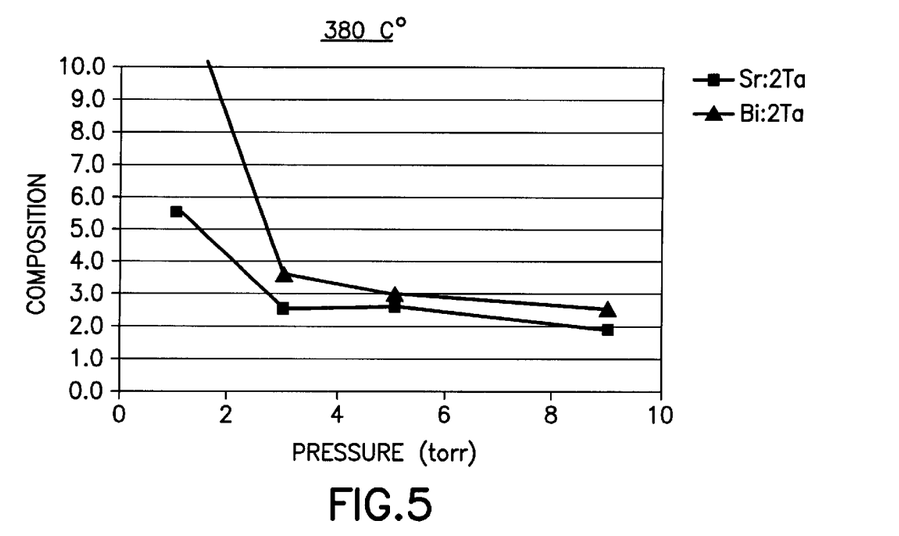
FIG. 5 is a graph of deposited film composition (Sr:2Ta, symbol "v;" Bi:2Ta, symbol "σ") as a function of pressure (Torr) at 380° C. for precursor solutions of 10:1 toluene: pmdeta solvent containing the precursors $Sr(thd)_2$-LBA, $Bi(thd)_3$, and $Ta(O-i-Pr)_4(thd)$.
Figure 6:
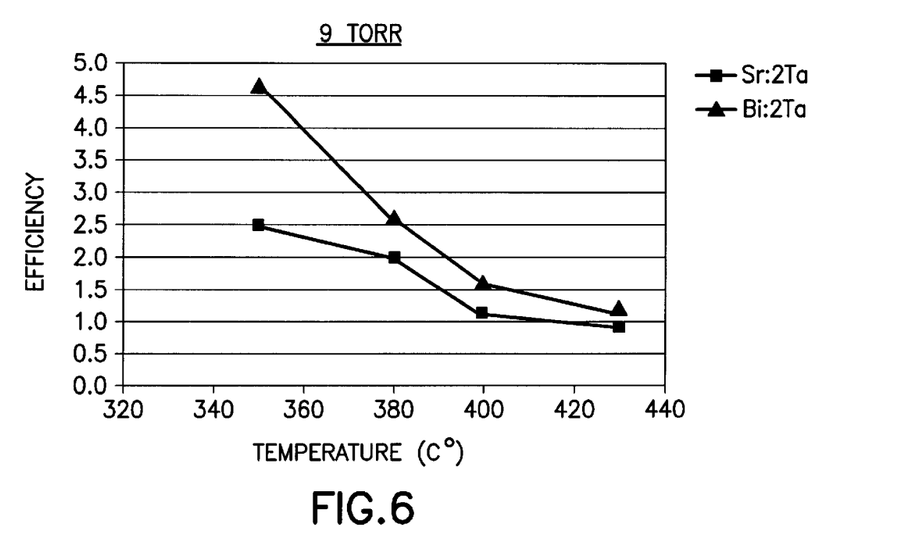
FIG. 6 is a graph of deposited film composition (Sr:2Ta, symbol "v;" Bi:2Ta, symbol "σ") as a function of temperature at 9 Torr for precursor solutions of 10:1 toluene: pmdeta solvent containing the precursors $Sr(thd)_2$-LBA, $Bi(thd)_3$, and $Ta(O-i-Pr)_4(thd)$.

FIG. 5 is a graph of deposited film composition (Sr:2Ta, symbol "v;" Bi:2Ta, symbol "σ") as a function of pressure (Torr) at 380° C. for precursor solutions of 10:1 toluene: pmdeta solvent containing the precursors $Sr(thd)_2$-LBA, $Bi(thd)_3$, and $Ta(O-i-Pr)_4(thd)$. FIG. 6 is a corresponding graph of deposited film composition (Sr:2Ta, symbol "v;" Bi:2Ta, symbol "σ") as a function of temperature at 9 Torr for precursor solutions of 10:1 toluene: pmdeta solvent containing the precursors $Sr(thd)_2$-LBA, $Bi(thd)_3$, and $Ta(O-i-Pr)_4(thd)$.

EXAMPLE 3

Figure 7:
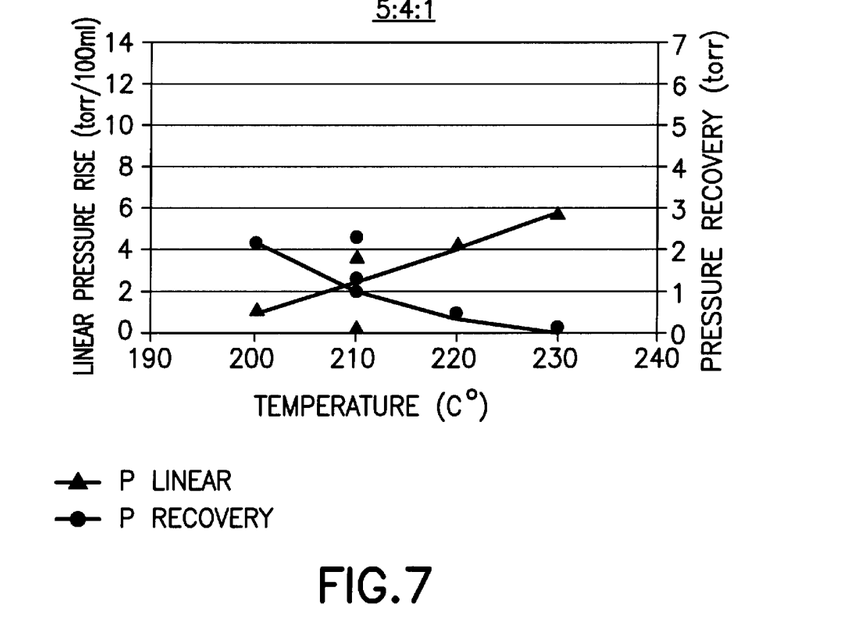
FIG. 7 is a graph of linear pressure rise, in Torr/100 milliliters of precursor solution, as a function of temperature, for a precursor solution of 5:4:1 octane:decane:pmdeta containing the precursors $Sr(thd)_2$-LBA, $Bi(thd)_3$, and $Ta(O-i-Pr)_4(thd)$.
Figure 8:
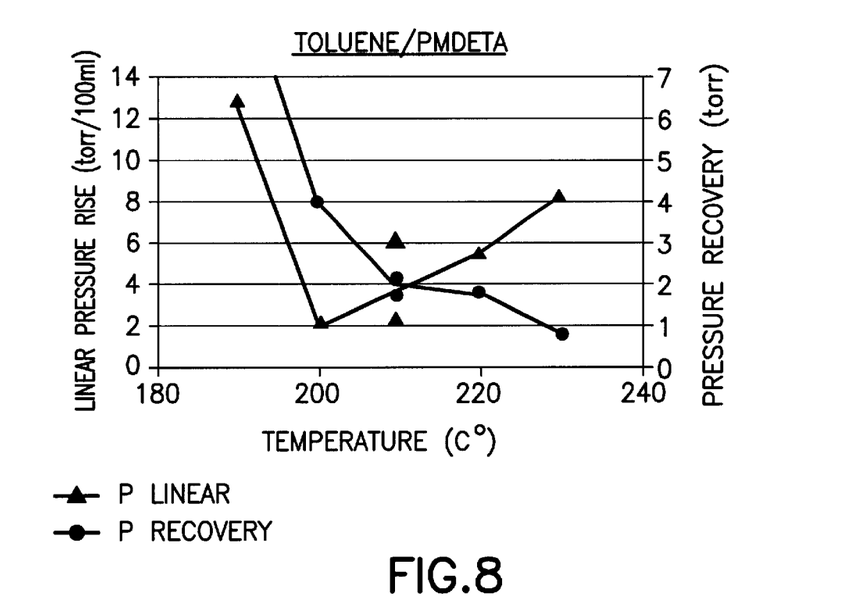
FIG. 8 is a graph of linear pressure rise, in Torr/100 milliliters of precursor solution, as a function of temperature, for a precursor solution of 10:1 toluene:pmdeta solvent containing the precursors $Sr(thd)_2$-LBA, $Bi(thd)_3$, and $Ta(O-i-Pr)_4(thd)$.

A precursor solution of 10:1 toluene: pmdeta solvent containing the precursors $Sr(thd)_2$-LBA, $Bi(thd)_3$, and Ta(O- i-Pr)$_4$(thd) was comparatively tested against a corresponding precursor solution of 5:4:1 octane:decane: pmdeta using a liquid delivery system of the type described in Example 1 equipped with a ¾" Vaporsource™ vaporizer, with a 300 standard cubic centimeters per minute flow rate of argon carrier gas, a precursor solution liquid flow rate of 0.3 milliliters per minute, and a porous frit vaporizer element having 40 micrometer diameter pores. Each experiment was performed by monitoring the pressure above the porous frit element as a function of time while maintaining the pressure downstream of the frit at 9 Torr using a throttle valve. The pressure above the frit increases as its pores clog with unevaporated precursor or decomposed precursor residue accumulates in the pores of the frit. Starting with a clean frit element, the rate of pressure rise decreases with time to some "pseudo-steady-state" which we define as the linear pressure rise. After 50 ml of solution have been delivered, the liquid flow is stopped and the pressure above the frit recovers to some steady-state value indicative of the total amount of decomposed precursor in the frit. The pressure drop from the point of turning off the liquid flow to this final steady-state condition is defined as the "pressure recovery". Linear pressure rise, in Torr/100 milliliters of precursor solution, and pressure recovery, in Torr, were determined for the respective precursor solutions, yielding the graphs of FIGS. 7 and 8. Large pressure recovery is indicative of slow evaporation of precursor from the frit with time which means that the vaporization temperature is lower than optimum. A high rate of linear pressure rise can be the result of the same if it is accompanied by the large pressure recovery. However, if a high rate of linear pressure rise is accompanied by a low pressure recovery, then it is probably indicative of precursor thermal decomposition to non-vaporizable species on the frit before it can be evaporated which means the vaporization temperature is higher than optimum. The similar shape and repeatability of data at 210° C. in FIGS. 7 and 8 indicate that the vaporization behavior is similar under these conditions.

EXAMPLE 4

A precursor solution of 10:1 toluene: pmdeta solvent containing the precursors Sr(thd)$_2$-LBA, Bi(thd)$_3$, and Ta(O-i-Pr)$_4$(thd) was comparatively tested against a corresponding precursor solution of 5:4:1 octane:decane: pmdeta solvent with the same precursors using a vaporizer and MOCVD reactor of the type described in Example 1. The ratios of metals in the solution was 43:33:24 Sr:Bi:Ta; the films were deposited in 9 Torr of process gas containing 76% O$_2$.

The incorporation efficiency of Sr, Bi and Ta were determined. Efficiency is the fraction of the precursor delivered to the process that is actually incorporated into the product SBT film.

Figure 9:
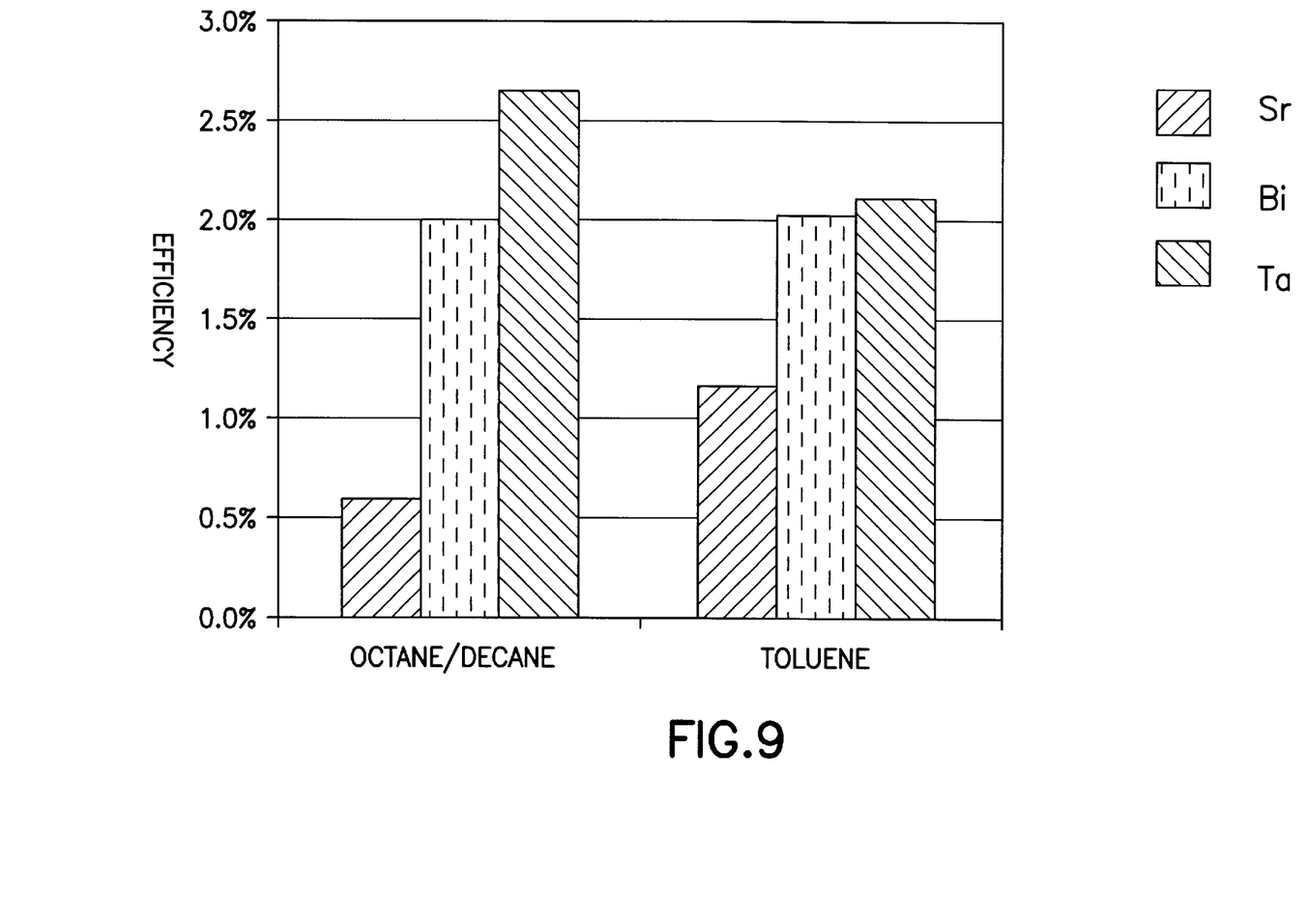
FIG. 9 is a graph of incorporation efficiencies of Sr, Bi and Ta, for (1) a precursor solution of 10:1 toluene: pmdeta solvent containing the precursors $Sr(thd)_2$-LBA, $Bi(thd)_3$, and $Ta(O-i-Pr)_4(thd)$, (2) a precursor solution of 5:4:1 octane:decane: pmdeta containing the precursors $Sr(thd)_2$-LBA, $Bi(thd)_3$, and $Ta(O-i-Pr)_4(thd)$, and (3) a precursor solution of tetrahydrofuran (THF), containing the precursors $Sr(thd)_2$-LBA, $Bi(thd)_3$, and $Ta(O-i-Pr)_4(thd)$.

Efficiencies for the above precursor solutions are shown in FIG. 9. These data show that the toluene-based composition concurrently yielded high strontium, bismuth and tantalum film incorporation efficiencies.

While the invention has been illustratively described herein with reference to various embodiments and disclosed features, it will be appreciated that the invention is not thus limited, but rather extends to and encompasses numerous variations, modifications and other embodiments. Accordingly, the invention is intended to be broadly construed and interpreted as including all such variations, modifications and other embodiments within the spirit and scope thereof, as hereinafter claimed.

What is claimed is:

1. A method of forming a material film on a substrate, comprising:

providing a precursor composition for at least one component of the material film;

volatilizing the precursor composition to yield a precursor vapor; and contacting the precursor vapor with the substrate to deposit said at least one component of the material film thereon;

wherein the precursor composition comprises (i) a solvent composition including toluene and a Lewis base, wherein toluene is present at a concentration of from about 75% to about 98% by volume, based on the total volume of toluene and the Lewis base, and (ii) a precursor species dissolved or suspended in the solvent composition.

2. The method of claim 1, wherein toluene is present in the precursor composition at a concentration of from about 90% to about 97% by volume, based on the total volume of toluene and Lewis base.

3. The method of claim 1, wherein the solvent composition has a boiling point in the range of from about 109.5 to about 112.0° C.

4. The method of claim 1, wherein toluene is present at a concentration of about 91% and the Lewis base is present at a concentration of about 9%.

5. The method of claim 1, wherein the Lewis base is selected from the group consisting of:

(a) amines and polyamines;

(b) N, S and O-containing aromatics;

(c) ligands of the formula:

wherein:
   G is —O—, —S—, or —NR—, wherein R is H or hydrocarbyl;

(d) crown ethers;

(e) thioethers;

(f) ammonia and other nitrogenous species; and (g) species of the formula: R$^0$O(C(R$^1$)$_2$C(R$^2$)$_2$O)$_n$R$^0$
   wherein:
   R$^0$=H, methyl, ethyl, n-propyl, cyanato, perfluoroethyl, perfluoro-n-propyl, or vinyl;
   R$^1$=H, F, or a sterically acceptable hydrocarbyl substituent;
   R$^2$=H, F, or a sterically acceptable hydrocarbyl substituent;
   n=2, 3, 4, 5, or 6; and
   each R$^0$, R$^1$, and R$^2$ may be the same as or different from the other R$^0$, R$^1$, and R$^2$, respectively.

6. The method of claim 1, wherein the Lewis base is selected from the group consisting of:

polyamines;

pyridines;

bipyridines;

alkylpyridines;

ammonia;

crown ethers; and species of the formula: $R^0O(C(R^1)_2C(R^2)_2O)_nR^0$ wherein:

$R^0$=H, methyl, ethyl, n-propyl, cyanato, perfluoroethylperfluoro-n-propyl, or vinyl;

$R^1$=H, F, or a sterically acceptable hydrocarbyl substituent;

$R^2$=H, F, or a sterically acceptable hydrocarbyl substituent;

n=2,3,4,5, or 6; and each $R^0$, $R^1$, and $R^2$ may be the same as or different from the other $R^0$, $R^1$, and $R^2$, respectively.

7. The method of claim 1, wherein the Lewis base is selected from the group consisting of: tetraglyme, tetrahydrofuran, bipydridine, ammonia, pyridine, alkylpyridine, 3-picoline, 18-crown-6 ethers, and amines/polyamines.

8. The method of claim 1, wherein the Lewis base is selected from the group consisting of: pentamethyldiethylenetriamine (PMDETA), diethylenetriamine (DETA). tetraethylenepentaamine (TEPA) and hexamethyltetraethylenepentaamine (HMTEPA).

9. The method of claim 1, wherein the precursor species comprises a precursor for a metal of a ferroelectric material.

10. The method of claim 1, wherein the precursor species comprises a precursor for strontium.

11. The method of claim 1, wherein the precursor species comprises a precursor for bismuth.

12. The method of claim 1, wherein the precursor species comprises a precursor for tantalum.

13. The method of claim 1, wherein the precursor species comprises a precursor for niobium.

14. The method of claim 1, wherein the precursor species comprises $Sr(thd)_2$-LBA where LBA is a Lewis base adducting species.

15. The method of claim 14, wherein the Lewis base adducting species is the same as the Lewis base of the solvent composition.

16. The method of claim 11, wherein the precursor species comprises $Bi(thd)_3$.

17. The method of claim 11, wherein the precursor species comprises $Bi(thd)_3$-LBA1 where LBA is a Lewis base adducting species.

18. The method of claim 17, wherein the Lewis base adducting species is the same as the Lewis base of the solvent composition.

19. The method of claim 1, wherein the precursor species comprises $Ta(O-i-Pr)_4(thd)$.

20. The method of claim 1, wherein the precursor species comprises $Nb(O-i-Pr)_4(thd)$.

21. The method of claim 1, wherein the precursor species comprises $Sr(thd)_2$-LBA, $Bi(thd)_3$, and $Ta(O-i-Pr)_4(thd)$, where LBA is a Lewis base adducting species that coordinatively complexes wit $Sr(thd)_2$.

22. The method of claim 21, wherein the Lewis base adducting species is the same as the Lewis base of the solvent composition.

23. The method of claim 1, wherein the precursor species comprises $Sr(thd)_2$-LBA, $Bi(thd)_3$-LBA, and $Ta(O-i-Pr)_4(thd)$, where LBA is a Lewis base adducting species that coordinatively complexes with $Sr(thd)_2$ and $Bi(thd)_3$.

24. The method of claim 23, wherein the Lewis base adducting species is the same as the Lewis base of the solvent composition.

25. The method of claim 1, having a total solution molarity of the precursor composition of from about 0.3 M to about 0.7 M.

* * * * *